(12) United States Patent
Townsend et al.

(10) Patent No.: US 10,478,245 B2
(45) Date of Patent: Nov. 19, 2019

(54) ENERGIZABLE ATTACHMENT FOR SURGICAL DEVICES

(71) Applicant: COVIDIEN LP, Mansfield, MA (US)

(72) Inventors: Jeffrey R. Townsend, Longmont, CO (US); Grant T. Sims, Littleton, CO (US)

(73) Assignee: Covidien LP, Mansfield, MA (US)

(*) Notice: Subject to any disclaimer, the term of this patent is extended or adjusted under 35 U.S.C. 154(b) by 405 days.

(21) Appl. No.: 14/566,329

(22) Filed: Dec. 10, 2014

(65) Prior Publication Data

US 2016/0166317 A1 Jun. 16, 2016

(51) Int. Cl.
A61B 18/14 (2006.01)
A61B 18/00 (2006.01)
A61B 18/12 (2006.01)

(52) U.S. Cl.
CPC ...... *A61B 18/1482* (2013.01); *A61B 18/1445* (2013.01); *A61B 2018/0063* (2013.01); *A61B 2018/00083* (2013.01); *A61B 2018/00172* (2013.01); *A61B 2018/00178* (2013.01); *A61B 2018/00601* (2013.01); *A61B 2018/126* (2013.01); *A61B 2018/1253* (2013.01); *A61B 2018/1422* (2013.01); *A61B 2018/1455* (2013.01); *A61B 2018/1467* (2013.01);
(Continued)

(58) Field of Classification Search
CPC .. A61B 2018/0091; A61B 2018/00916; A61B 2018/00922; A61B 2018/144; A61B 2018/1475; A61B 2018/1495
See application file for complete search history.

(56) References Cited

U.S. PATENT DOCUMENTS 5,312,391 A 5/1994 Wilk
5,318,589 A 6/1994 Lichtman
(Continued)

FOREIGN PATENT DOCUMENTS

CN 101401738 A 4/2009
CN 102688096 A 9/2012
(Continued)

OTHER PUBLICATIONS

Australian office action issued in corresponding application No. 2015245029 dated Jun. 20, 2016.
(Continued)

*Primary Examiner* — Ronald Hupczey, Jr.
(74) *Attorney, Agent, or Firm* — Carter, DeLuca & Farrell LLP

(57) ABSTRACT

An energizable surgical attachment is configured for positioning about a shaft of a surgical instrument. The energizable surgical attachment includes an outer sheath defining a lumen extending longitudinally through the outer sheath, an energizable rod member coupled to the outer sheath, a connector attachment electrically coupled to the energizable rod member, and at least one o-ring disposed within the lumen of the outer sheath. At least a portion of the energizable rod member extends distally from the distal end of the outer sheath. The o-ring(s) are configured to establish a fluid-tight seal between the outer sheath and the shaft of the surgical instrument and to bias the outer sheath towards a stationary position relative to the shaft of the surgical instrument.

6 Claims, 9 Drawing Sheets

(52) U.S. Cl.
CPC ............ *A61B 2018/1475* (2013.01); *A61B 2018/1495* (2013.01)

(56) References Cited

U.S. PATENT DOCUMENTS

| | | | |
|---|---|---|---|
| 5,324,254 A | 6/1994 | Phillips | |
| 5,364,395 A * | 11/1994 | West, Jr. | A61B 17/32002 604/22 |
| 5,401,274 A | 3/1995 | Kusunoki | |
| 5,445,638 A | 8/1995 | Rydell et al. | |
| 5,458,598 A | 10/1995 | Feinberg et al. | |
| 5,499,998 A * | 3/1996 | Meade | A61B 17/29 606/207 |
| 5,556,397 A * | 9/1996 | Long | A61B 18/1402 606/48 |
| 5,735,873 A | 4/1998 | MacLean | |
| 5,792,164 A | 8/1998 | Lakatos et al. | |
| 5,810,809 A * | 9/1998 | Rydell | A61B 17/32002 604/22 |
| 5,893,863 A | 4/1999 | Yoon | |
| 5,919,202 A | 7/1999 | Yoon | |
| 6,004,320 A * | 12/1999 | Casscells | A61B 17/32002 606/170 |
| 6,086,583 A * | 7/2000 | Ouchi | A61B 1/00089 604/35 |
| 6,113,596 A | 9/2000 | Hooven et al. | |
| 6,156,009 A | 12/2000 | Grabek | |
| 6,190,386 B1 | 2/2001 | Rydell | |
| 6,270,497 B1 | 8/2001 | Sekino et al. | |
| 6,299,625 B1 | 10/2001 | Bacher | |
| 6,387,094 B1 | 5/2002 | Eitenmuller | |
| 6,551,313 B1 | 4/2003 | Levin | |
| 6,679,882 B1 | 1/2004 | Kornerup | |
| 6,808,525 B2 | 10/2004 | Latterell et al. | |
| 6,942,662 B2 | 9/2005 | Goble et al. | |
| 7,033,356 B2 | 4/2006 | Latterell et al. | |
| 7,063,699 B2 | 6/2006 | Hess et al. | |
| 7,128,254 B2 | 10/2006 | Shelton, IV et al. | |
| 7,232,440 B2 | 6/2007 | Dumbauld et al. | |
| 7,367,976 B2 | 5/2008 | Lawes et al. | |
| 7,402,162 B2 | 7/2008 | Ouchi | |
| 7,445,621 B2 | 11/2008 | Dumbauld et al. | |
| 7,510,562 B2 | 3/2009 | Lindsay | |
| 7,588,570 B2 | 9/2009 | Wakikaido et al. | |
| 7,658,311 B2 | 2/2010 | Boudreaux | |
| 7,758,577 B2 | 7/2010 | Nobis et al. | |
| 7,815,636 B2 | 10/2010 | Ortiz | |
| 7,819,872 B2 | 10/2010 | Johnson et al. | |
| 8,257,352 B2 | 9/2012 | Lawes et al. | |
| 8,353,437 B2 | 1/2013 | Boudreaux | |
| 2002/0049442 A1 | 4/2002 | Roberts et al. | |
| 2004/0236326 A1 | 11/2004 | Schulze et al. | |
| 2005/0187547 A1 | 8/2005 | Sugi | |
| 2005/0251134 A1 | 11/2005 | Woloszko et al. | |
| 2008/0045859 A1 | 2/2008 | Fritsch et al. | |
| 2008/0215050 A1 | 9/2008 | Bakos | |
| 2009/0125026 A1 | 5/2009 | Rioux et al. | |
| 2009/0125027 A1 | 5/2009 | Fischer | |
| 2009/0131974 A1 | 5/2009 | Pedersen et al. | |
| 2009/0254084 A1 | 10/2009 | Naito | |
| 2010/0185196 A1 | 7/2010 | Sakao et al. | |
| 2010/0185197 A1 | 7/2010 | Sakao et al. | |
| 2010/0292690 A1 | 11/2010 | Livneh | |
| 2011/0087218 A1 | 4/2011 | Boudreaux et al. | |
| 2011/0130757 A1 | 6/2011 | Horlle et al. | |
| 2011/0264093 A1 | 10/2011 | Schall | |
| 2012/0330351 A1 | 12/2012 | Friedman et al. | |
| 2014/0005663 A1 * | 1/2014 | Heard | A61B 18/1445 606/41 |
| 2014/0135763 A1 * | 5/2014 | Kappus | A61B 18/1445 606/52 |
| 2014/0276797 A1 | 9/2014 | Batchelor et al. | |

FOREIGN PATENT DOCUMENTS

| | | |
|---|---|---|
| EP | 2502550 A2 | 9/2012 |
| EP | 2679185 A1 | 1/2014 |
| JP | 2000139944 A | 5/2000 |

OTHER PUBLICATIONS

Extended European search report issued in corresponding application No. 151913308.8 dated Apr. 14, 2016.
Chinese Office Action including translation issued in corresponding application No. 201510698659.3 dated Aug. 1, 2017.
Second Chinese Office Action issued in corresponding application No. 201510698659.3 dated May 16, 2018 with English Translation.
European examination report issued in corresponding EP application No. 15191330.8 dated Oct. 16, 2018, 5 pages.
Chinese Office Action issued in corresponding application Chinese Application No. 201510698659.3 dated Dec. 11, 2018 with English translation,.

* cited by examiner

ENERGIZABLE ATTACHMENT FOR SURGICAL DEVICES

BACKGROUND

Technical Field

The present disclosure relates to surgical devices and, more particularly, to an energizable attachment for use with surgical devices to facilitate treating tissue.

Background of Related Art

An endoscopic surgical instrument typically includes a housing having a shaft extending therefrom and an end effector assembly disposed at a distal end of the shaft. An endoscopic surgical forceps, for example, includes an end effector assembly having jaw members and relies on mechanical action between the jaw members to grasp, clamp, and/or constrict tissue. Electrosurgical forceps utilize both mechanical clamping action and electrical energy to affect hemostasis by heating tissue to coagulate and/or cauterize tissue. Certain surgical procedures require more than simply cauterizing tissue and rely on the unique combination of clamping pressure, precise electrosurgical energy control, and gap distance (i.e., distance between the opposing jaw members when closed about tissue) to "seal" tissue. In some surgical procedures, it may be beneficial to use both bipolar and monopolar instrumentation, e.g., procedures where it is necessary to dissect through one or more layers of tissue, or otherwise treat such tissue, in order to reach underlying tissue(s) to be sealed or otherwise treated.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with the present disclosure, an energizable surgical attachment configured for positioning about a shaft of a surgical instrument is provided. The energizable surgical attachment includes an outer sheath defining a proximal end and a distal end and including an internal surface defining a lumen extending longitudinally through the outer sheath, an energizable rod member coupled to the outer sheath, a connector attachment, and at least one o-ring. At least a portion of the energizable rod member extends distally from the distal end of the outer sheath. The connector attachment is disposed towards the proximal end of the outer sheath and is electrically coupled to the energizable rod member. The at least one o-ring is disposed within the lumen of the outer sheath and coupled to the internal surface of the outer sheath. The at least one o-ring is configured to establish a fluid-tight seal between the outer sheath and the shaft of the surgical instrument and to bias the outer sheath towards a stationary position relative to the shaft of the surgical instrument.

In an aspect of the present disclosure, the outer sheath is electrically insulative.

In another aspect of the present disclosure, the energizable surgical attachment further includes a connector assembly configured to releasably connect to the connector attachment.

In yet another aspect of the present disclosure, the connector assembly includes a plug adapted to connect to a source of energy.

In still another aspect of the present disclosure, the connector assembly includes a hand-activated switch.

In another aspect of the present disclosure, the hand-activated switch is configured to couple to the surgical instrument.

In still yet another aspect of the present disclosure, the connector assembly is configured to supply energy to the energizable rod member via a lead wire extending therebetween.

In another aspect of the present disclosure, the energizable rod member is configured to supply energy to tissue to treat tissue.

In yet another aspect of the present disclosure, the energizable rod member is configured to supply energy to tissue.

In still another aspect of the present disclosure, the energizable rod member defines an L-hook shaped configuration.

A surgical system is also provided in accordance with the present disclosure. The surgical system includes a surgical instrument having a housing, a shaft extending distally from the housing, and an end effector assembly disposed at a distal end of the shaft. The surgical system further includes an energizable surgical attachment which may be configured similarly to any of the aspects detailed above. The outer sheath of the energizable surgical attachment is configured for positioning about the shaft of the surgical instrument. The at least one o-ring of the energizable surgical attachment is configured to establish a fluid-tight seal between the outer sheath and the shaft of the surgical instrument and to bias the outer sheath towards a stationary position relative to the shaft of the surgical instrument.

In an aspect of the present disclosure, the energizable surgical attachment is movable relative to the surgical instrument between a retracted position, wherein the energizable surgical attachment is disposed proximally of the end effector assembly, and a deployed position, wherein the outer sheath is disposed about the end effector assembly and the energizable rod member extends distally beyond the distal end of the end effector assembly.

In another aspect of the present disclosure, the transition of the energizable surgical attachment between the retracted position and the deployed position is performed manually upon sufficient urging to overcome the bias of the outer sheath towards the stationary position relative to the shaft of the surgical instrument.

In yet another aspect of the present disclosure, the outer sheath includes a connector attachment extending from the outer sheath and electrically coupled to the energizable rod member.

In still another aspect of the present disclosure, a connector assembly configured to releasably couple to the connector attachment is provided. The connector assembly may include a hand-activated switch and a plug adapted to connect to a source of energy. The hand-activated switch may be configured to couple to the surgical instrument.

BRIEF DESCRIPTION OF THE DRAWINGS

Various aspects and features of the present disclosure are described herein with reference to the drawings wherein.

DETAILED DESCRIPTION

Detailed below and illustrated in FIGS. 1A-2 and 4A-7B are various embodiments of energizable surgical attachments configured for use with endoscopic surgical instruments to facilitate treating tissue. Although the various embodiments of energizable surgical attachments provided herein are described and illustrated in use in conjunction with endoscopic surgical forceps 10 (FIG. 3), it is contemplated that the energizable surgical attachments of the present disclosure are equally applicable for use with any other suitable endoscopic surgical instrument to facilitate treating tissue. Further, to the extent consistent, any of the embodiments detailed hereinbelow, although described separately, may include any or all of the features of any or all of the other embodiments of the present disclosure.

Figure 1A:
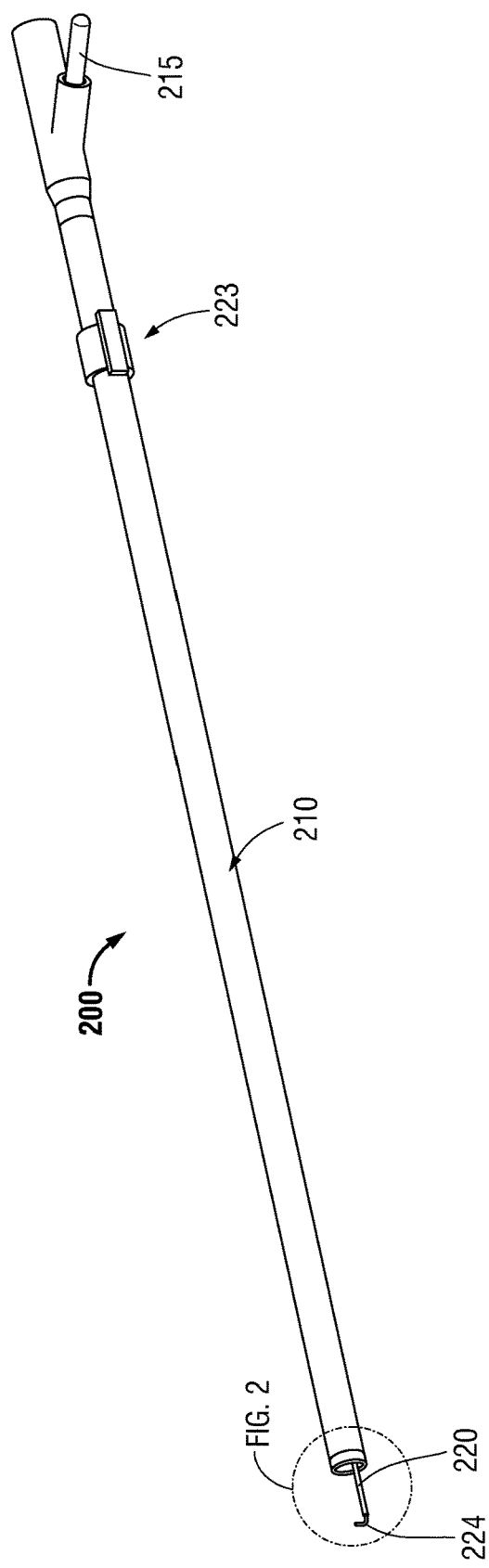
FIG. 1A is a side, perspective view of an energizable surgical attachment provided in accordance with the present disclosure.

Referring to FIG. 1A, an energizable surgical attachment provided in accordance with the present disclosure is shown generally identified by reference numeral 200. Energizable surgical attachment 200 generally includes an outer sheath 210, a connector attachment 215 located towards the proximal end of the outer sheath 210, and an energizable rod member 220 which extends through or within outer sheath 210. As detailed below, the energizable surgical attachment 200 is configured for positioning about a shaft of a surgical instrument, e.g., shaft 12 of surgical forceps 10 (FIG. 3), and is manually moveable relative thereto to facilitate treating tissue.

Figure 3:
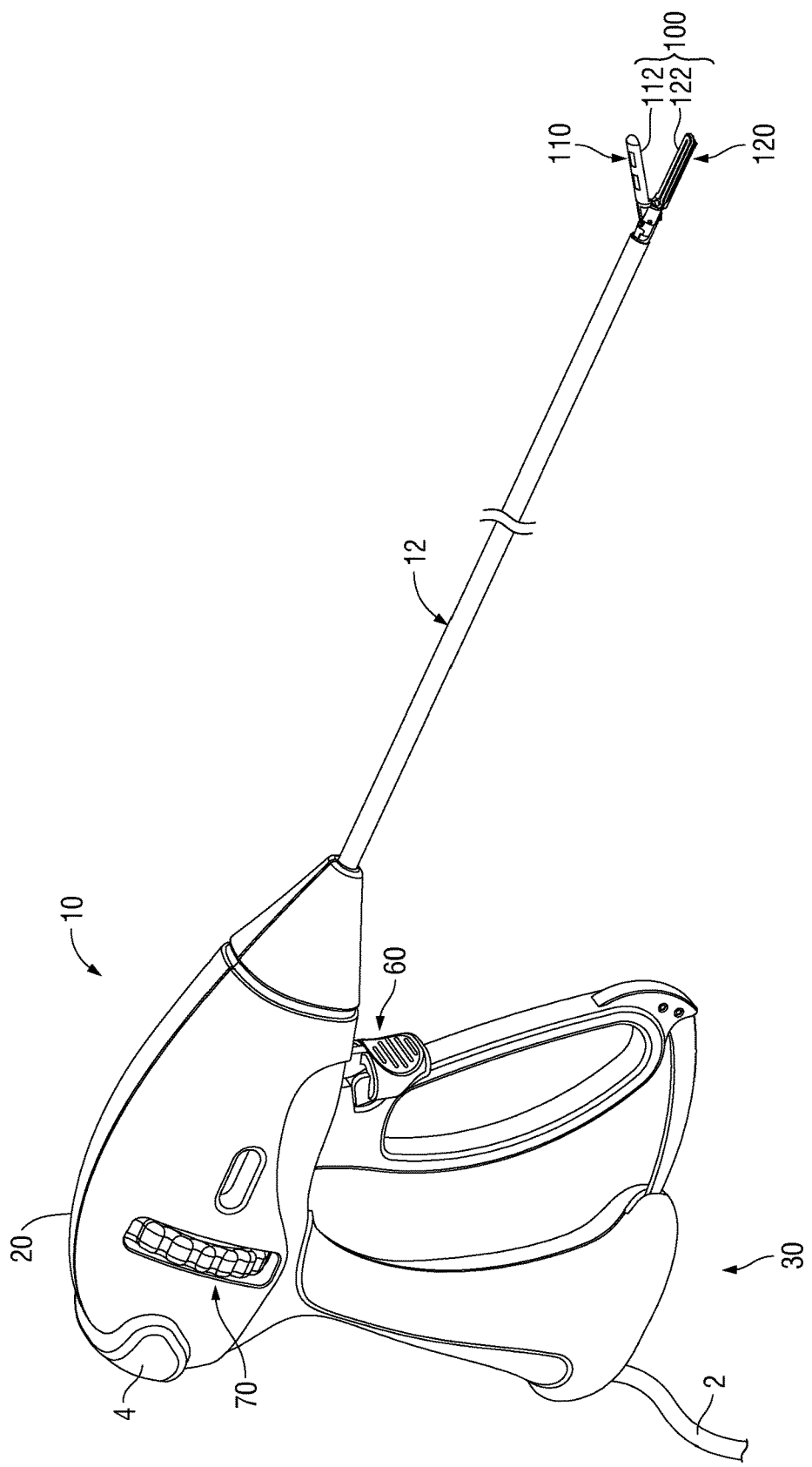
FIG. 3 is a front, side, perspective view of a surgical instrument configured for use with the energizable surgical attachments of the present disclosure.

The outer sheath 210 defines an elongated, generally tubular configuration and, as noted above, is configured for positioning about a shaft of an endoscopic instrument, e.g., shaft 12 of forceps 10 (FIG. 3). The internal and external surfaces of the outer sheath 210 may be formed from or coated with an electrically-insulative material. The outer sheath 210 defines a suitable length to enable slidable movement about the shaft of the endoscopic instrument between a retracted position and a deployed position, as detailed below, and such that the distal end of the outer sheath 210 is capable of extending into an internal surgical site while the proximal end of the outer sheath 210 remains externally disposed to enable manipulation thereof by the user. More specifically, the outer sheath 210 is configured to be gripped by a user and manually slid longitudinally along the shaft of the endoscopic instrument between retracted (FIG. 4A) and deployed (FIG. 7A) positions. The outer sheath 210 may further be manually rotatable about the shaft of the endoscopic instrument. The outer sheath 210 additionally includes one or more o-rings 218 (FIGS. 4A and 4B) disposed therein, the importance of which are detailed below.

The connector attachment 215 is located towards the proximal end of the energizable surgical attachment 200 and branches off from the outer sheath 210. The connector attachment 215 is configured to facilitate connection of one or more plugs 213, 214 (see FIG. 1B) thereto for enabling the selective supply of energy to energizable rod member 220, as detailed below.

Figure 1B:
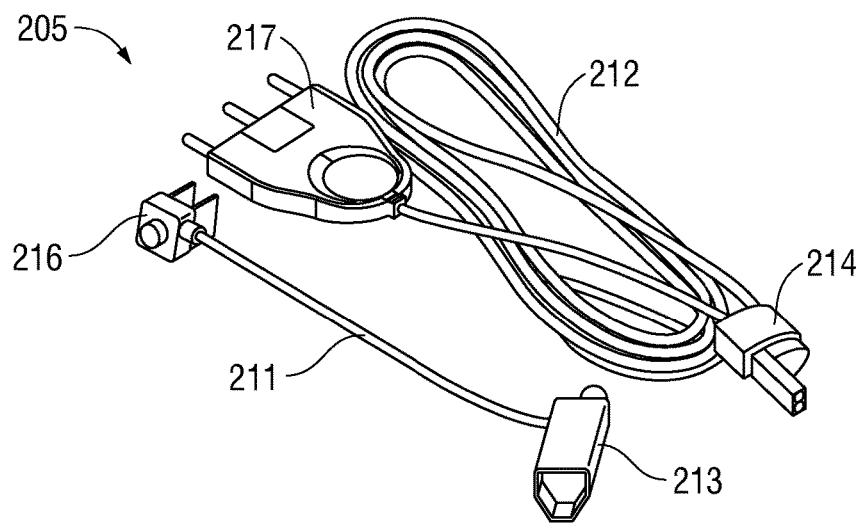
FIG. 1B is view of a connector provided in accordance with the present disclosure and configured for use with the energizable surgical attachments of the present disclosure.
Figure 2:
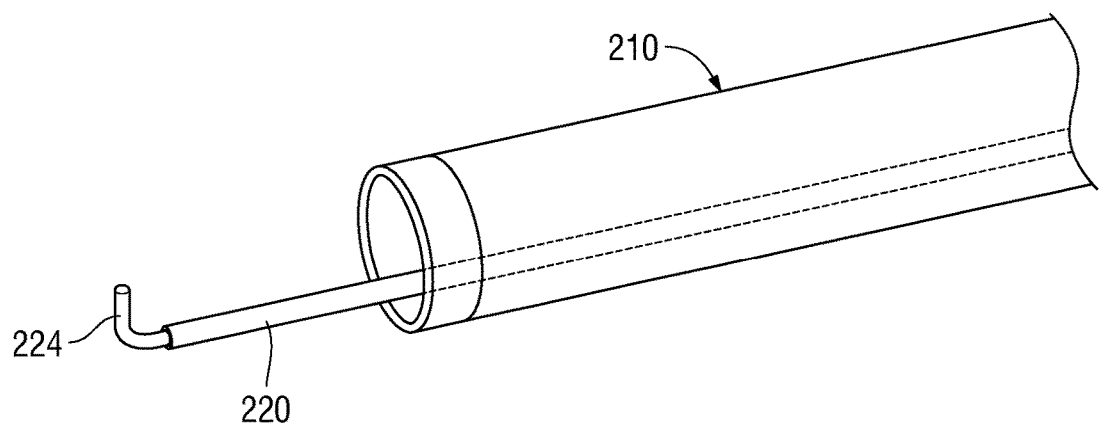
FIG. 2 is an enlarged view of the area of detail indicated as "2" in FIG. 1A.
Figure 4A:
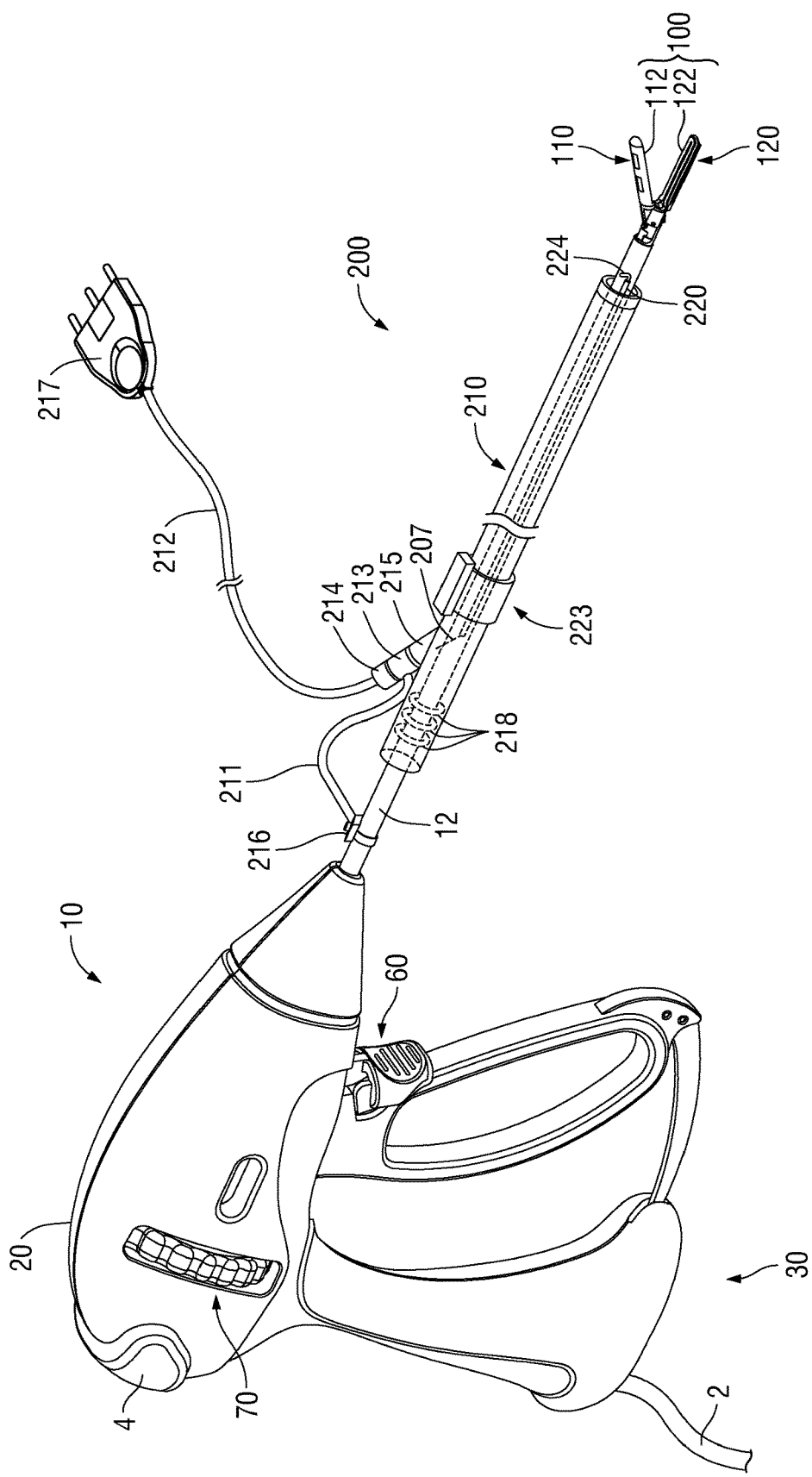
FIG. 4A is a front, side, perspective view of an energizable surgical attachment of the present disclosure disposed about the surgical instrument of FIG. 3 in a retracted position, with the connector of FIG. 1B coupled to the shaft of the surgical instrument.
Figure 4B:
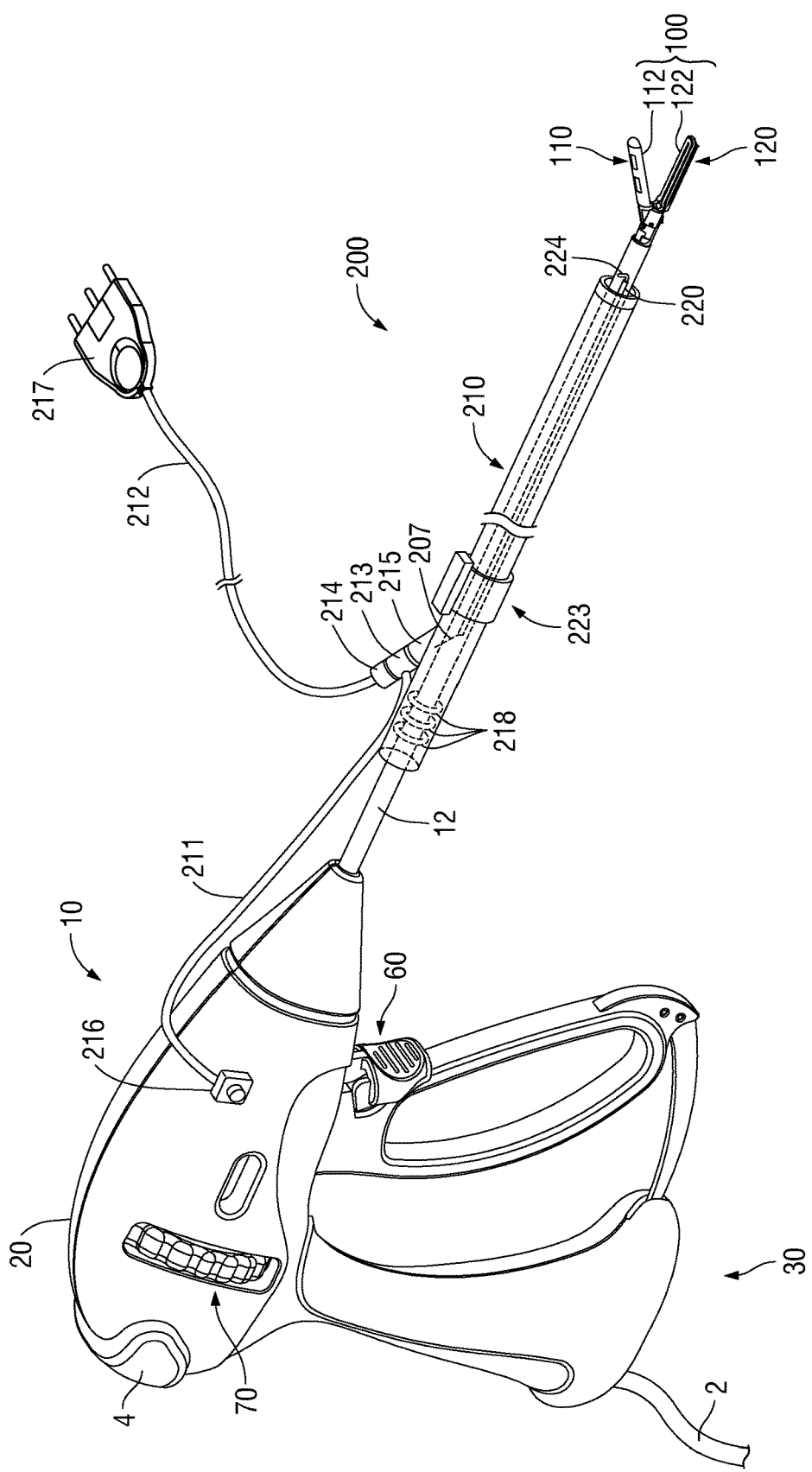
FIG. 4B is a front, side, perspective view of an energizable surgical attachment of the present disclosure disposed about the surgical instrument of FIG. 3 in the retracted position, with the connector of FIG. 1B coupled to the housing of the surgical instrument.

With additional reference to FIG. 2, the energizable rod member 220 extends distally from outer sheath 210 ultimately defining an electrically-conductive distal tip 224. Energizable rod member 220 and, more specifically, distal tip 224 thereof, functions as the active electrode of energizable surgical attachment 200. The distal tip 224 of energizable rod member 200 may be hook-shaped (as shown), or may define any other suitable configuration, e.g., linear, ball, circular, angled, needle, etc. The exposed portion of energizable rod member 200 that is proximal of distal tip 224 may be coated with an electrically-insulative material. The proximal portion of energizable rod member 220 may be configured to extend through or within outer sheath 210 to ultimately couple to connector attachment 215, or may terminate at or further distally within outer sheath 210 and be coupled to connector attachment 215 via one or more lead wires 207 (FIGS. 4A and 4B). Energy may be supplied from connector attachment 215, through energizable rod member 220, to distal tip 224 to treat tissue, e.g., via activation of a hand-activated switch 216 (see FIG. 1B) or other suitable actuator. The energy supplied to tissue may be monopolar electrical energy, ultrasonic energy, thermal energy, light energy, argon gas energy, or any other suitable energy. Energizable rod member 220 may be positioned on one side of the outer sheath 210 (as provided for illustrative purposes in FIGS. 1A, 2, 5, 6B, and 7B), on the other side of the outer sheath 210 (as provided for illustrative purposes in FIGS. 4A, 4B, 6A, and 7A), or may be positioned on the top, bottom, or at other suitable position therebetween.

Energizable rod member 200 may be fixedly secured within outer sheath 210. Alternatively, an energizable rod member deployment actuator 223 may be disposed on outer sheath 210 and coupled to energizable rod member 200 via any suitable mechanism (not shown). Energizable rod member deployment actuator 223 is located towards the proximal end of outer sheath 210 and is selectively slidable along outer sheath 210 to deploy the energizable rod member 220 from or further beyond the distal end of outer sheath 210 and retract the energizable rod member 220 into or closer to the distal end of outer sheath 210.

Referring now to FIG. 1B, a connector assembly 205 configured for releasable connection with connector attachment 215 is provided. The connector assembly 205 includes hand-activated switch 216, which is connected to a first connector 213 via a cable 211, and a plug 217, which is connected to a second connector 214 via a cable 212. First and second connectors 213, 214, respectively, are configured to releasably couple with connector attachment 215 for enabling the selective supply of energy from an energy source (not shown, to which plug 217 is connected), through wire 212 and the lead wire 207 (FIGS. 4A and 4B), to the energizable rod member 220, e.g., upon activation of hand-activated switch 216.

The hand-activated switch 216 is configured to switch on and off the flow of energy to the connector attachment 215 and, thus, to the lead wire 207 (FIGS. 4A and 4B) and, ultimately, the energizable rod member 220. The hand-activated switch 216 may be configured to engage the housing of the endoscopic surgical instrument, e.g., housing 20 of forceps 10 (see FIG. 4A), or may be configured to engage the shaft of the endoscopic surgical instrument, e.g., shaft 12 of forceps 10 (see FIG. 4B), via an adhesive, snap-on connector, or other suitable engagement structure or mechanism, or may alternatively be configured to be held by or attached to a user. Other connectors assemblies for coupling to connector attachment 215 are also contemplated such as, for example, those associated with footswitches and other switching assemblies.

Referring to FIG. 3, one embodiment of a surgical instrument configured for use with energizable surgical attachment 200 is identified as surgical forceps 10. Surgical forceps 10 generally includes a housing 20, a handle assembly 30, a trigger assembly 60, a rotating assembly 70, and an end effector assembly 100. Surgical forceps 10 further includes a shaft 12 having a distal end that mechanically engages end effector assembly 100 and a proximal end that extends into housing 20. Surgical forceps 10 also includes an electrosurgical cable 2 that connects forceps 10 to a generator (not shown) or other suitable energy source, although forceps 10 may alternatively be configured as a handheld, battery powered instrument. Cable 2 includes wires (not shown) extending there through that have sufficient length to extend through shaft 12 in order to provide electrical energy to at least one of the electrically-conductive surfaces 112, 122 of jaw members 110, 120, respectively, of end effector assembly 100, e.g., upon activation of activation switch 4. Rotating assembly 70 is rotatable in either direction to rotate end effector assembly 100 relative to housing 20. Housing 20 houses the internal working components of forceps 10.

Handle assembly 30 includes a moveable handle 40 that is ultimately connected to a drive assembly (not shown) disposed within housing 20 that, together, mechanically cooperate to impart movement of jaw members 110, 120 between a spaced-apart position and an approximated position to grasp tissue between surfaces 112, 122 of jaw members 110, 120, respectively. More specifically, movable handle 40 is actuatable from an initial position, corresponding to the spaced-apart position of the jaw member 110, 120, to a depressed position corresponding to the approximated position of the jaw members 110, 120. In some embodiments, a knife assembly 180 (not shown) disposed within shaft 12 is provided including a knife that is selectively extendable between jaw members 110, 120, e.g., via activation of trigger assembly 60 to cut tissue grasped between surface 112, 122.

Figure 5:
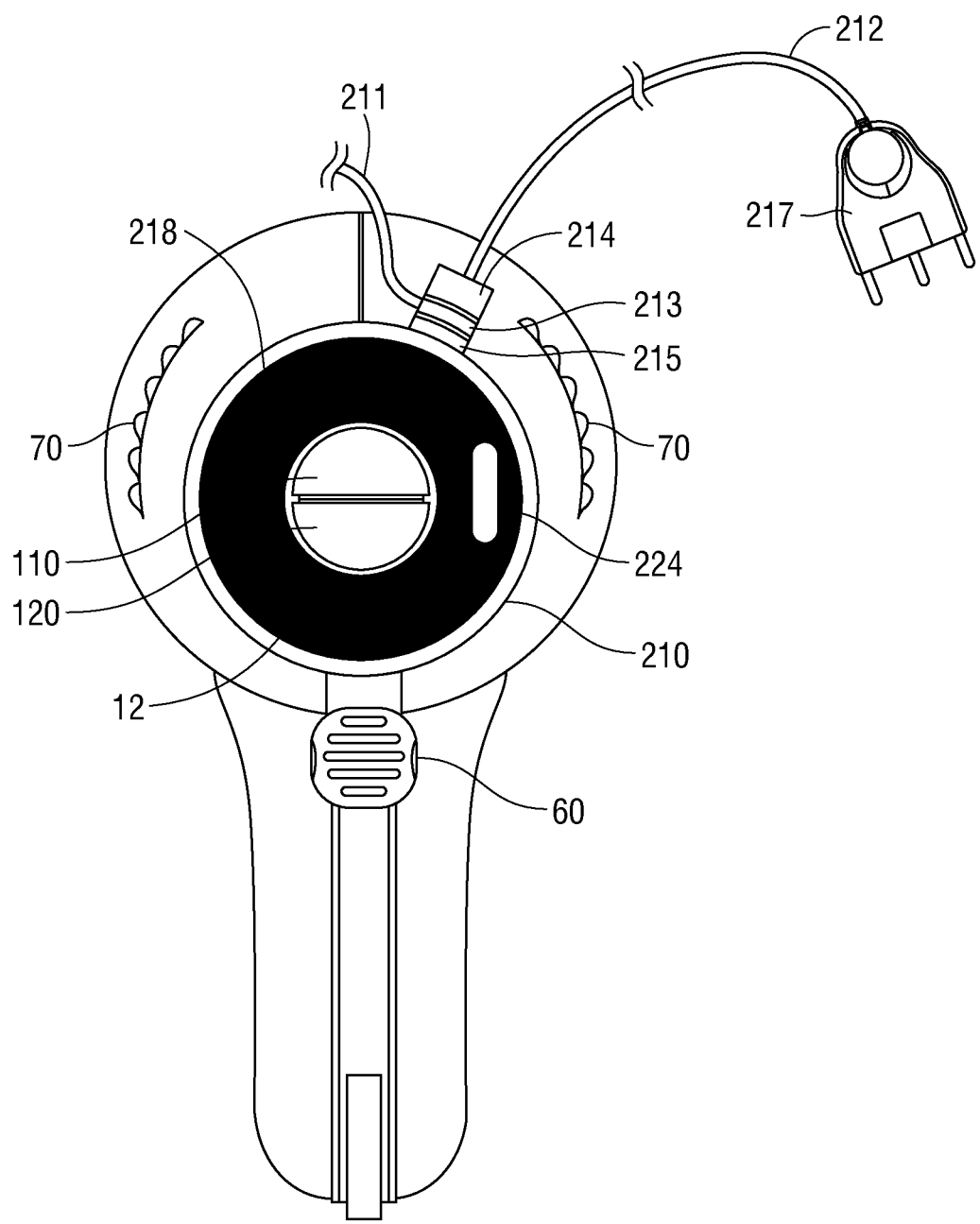
FIG. 5 is a front view of an energizable surgical attachment of the present disclosure disposed about the surgical instrument of FIG. 3 and having the connector of FIG. 1B coupled thereto.
Figure 6A:
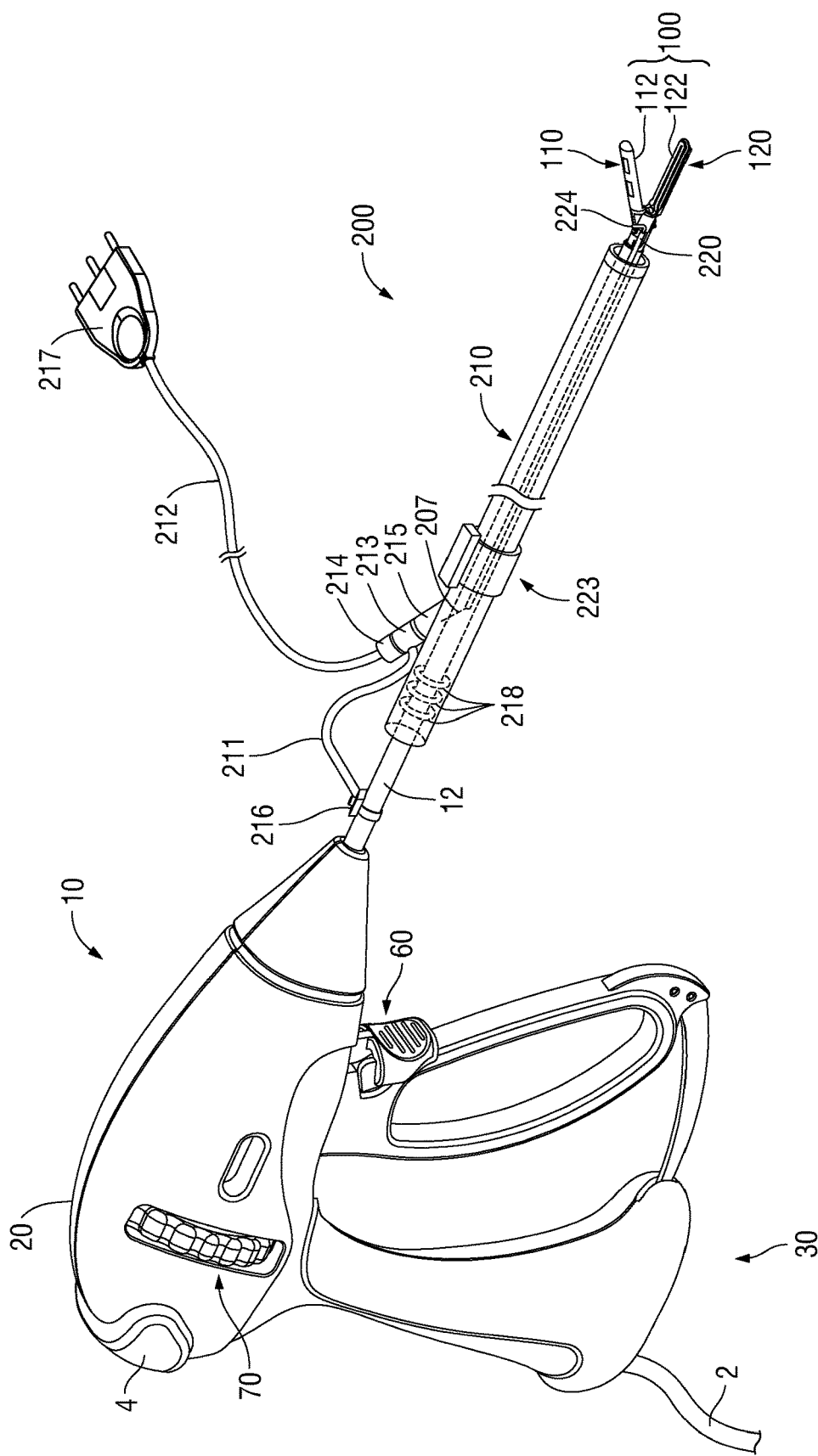
FIG. 6A is a front, side, perspective view of an energizable surgical attachment of the present disclosure disposed about the surgical instrument of FIG. 3 in a partially deployed position, with the connector of FIG. 1B located on the shaft of the surgical instrument.
Figure 6B:
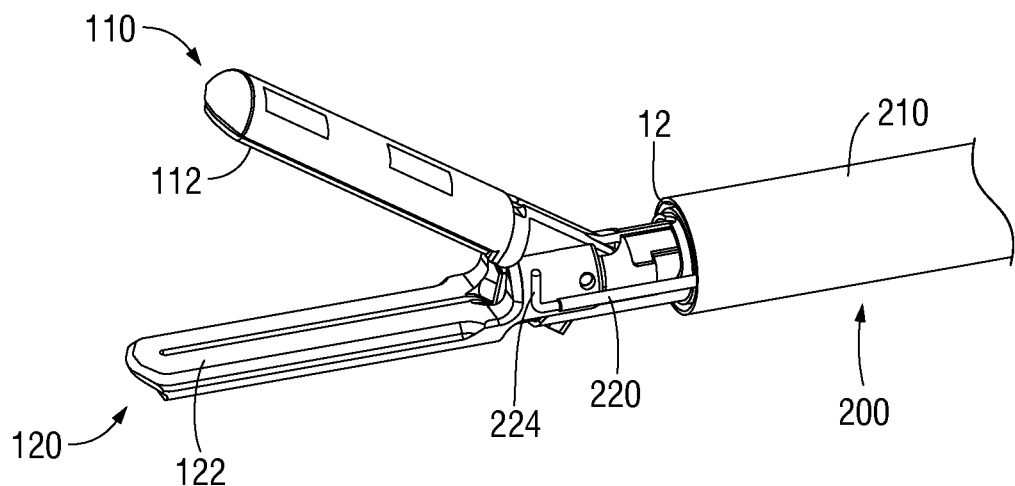
FIG. 6B is an enlarged, perspective view of the distal end of an energizable surgical attachment of the present disclosure disposed about the surgical instrument of FIG. 3 in a partially deployed position.
Figure 7B:
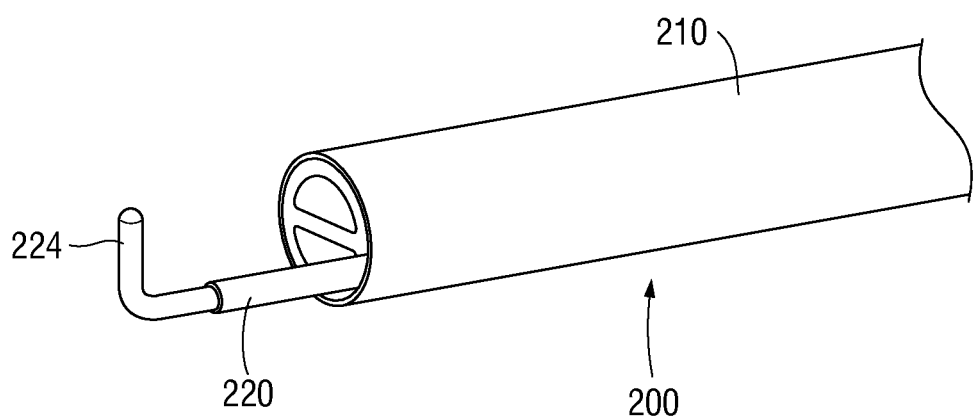
FIG. 7B is an enlarged, perspective view of the distal end of an energizable surgical attachment of the present disclosure disposed about the surgical instrument of FIG. 3 in a fully deployed position.
Figure 7A:
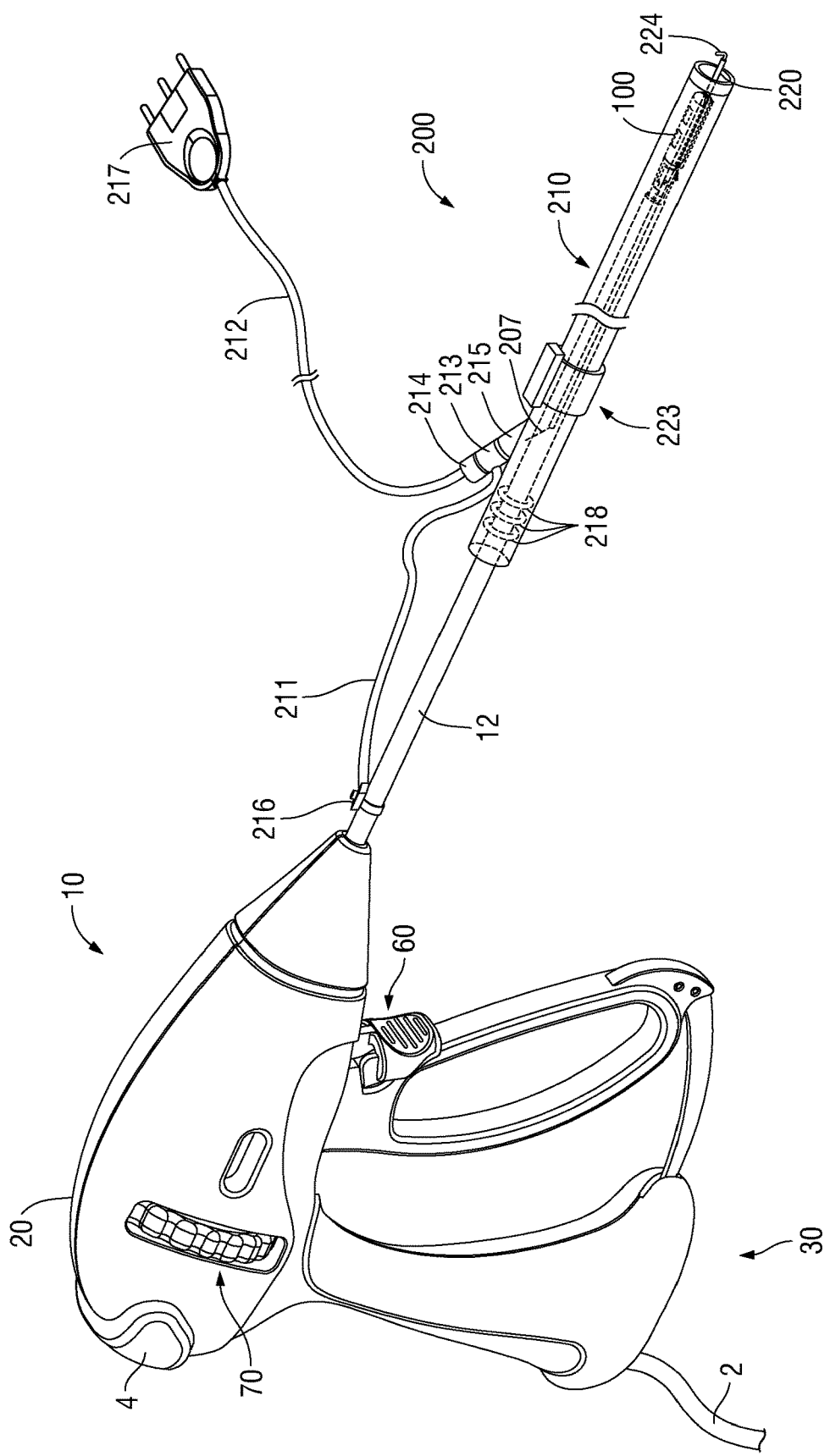
FIG. 7A is a front, side, perspective view of an energizable surgical attachment of the present disclosure disposed about the surgical instrument of FIG. 3 in a fully deployed position, with the connector of FIG. 1B located on the shaft of the surgical instrument.

Referring now to FIGS. 4A, 4B, and 5, the energizable surgical attachment 200 is shown disposed about shaft 12 of surgical forceps 10 in a retracted position such that the energizable rod member 220 does not extend distally beyond end effector assembly 100 and such that end effector assembly 100 is exposed beyond the outer sheath 210 to enable grasping and treating of tissue therewith. As shown in FIG. 4A, connector assembly 205 is coupled to connector attachment 215 and hand-activated switch 216 is located on shaft 12. As shown in FIG. 4B, connector assembly 205 is coupled to connector attachment 215 and hand-activated switch 216 is located on housing 20.

The outer sheath 210, as noted above, includes one or more o-rings 218 that are coupled to the inner surface of the outer sheath 210 and extend into the inner lumen defined by the outer sheath 210. The o-rings 218 are located towards the proximal end of the outer sheath 210 and define apertures having inner diameters smaller than the outer diameter of the shaft 12 of the forceps 10 (or other surgical instrument configured for insertion therethrough) such that the plurality of o-rings 218 are compressed upon positioning of the energizable surgical attachment 200 about the shaft 12 to create a fluid tight seal within the inner lumen of the outer sheath 210, thereby preventing the escape of insufflation gas therebetween. The o-rings may be inset into grooves, slots or fitably attached within the outer sheath 210. The plurality of o-rings 218 also create a friction between the inner surface of the outer sheath 210 and the outer surface of the shaft 12 thereby creating a movement bias between the outer sheath 210 and shaft 12 such that energizable surgical attachment 200 is frictionally retained in position relative to forceps 10 in the absence of suitable urging to overcome such bias. As can be appreciated, the sizes of the o-rings 218 used for the energizable surgical attachment 200 vary depending on the size of the shaft of the surgical instrument used therewith and/or other factors such as the fluid tight seal requirement or movement bias requirement.

Referring to FIGS. 4A and 6A-7B, in order to deploy the energizable surgical attachment 200, the outer sheath 210 is slid distally about the shaft 12, with sufficient urging to overcome the bias of the o-rings 218, from the retracted position (FIG. 4A), through a partially-deployed position (FIGS. 6A and 6B), to a fully deployed position (FIGS. 7A and 7B), wherein the energizable member 220 extends beyond the distal end of end effector assembly 100 and the outer sheath 210 is disposed about the end effector assembly 100. In addition, prior to, during, or after the deployment of the energizable surgical attachment 200, the outer sheath 210 may be rotated relative to shaft 12 to rotate energizable rod member 220 to a desired orientation. Thereafter, energy may be supplied to energizable rod member 220, e.g., via activation of hand-activated switch 216, to treat tissue using distal tip 225 of energizable rod member 220. Retraction of the energizable surgical attachment 200 is effected in the opposite manner as the deployment.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical system, comprising:
   a surgical instrument, including:
      a housing;
      a shaft extending distally from the housing; and
      an end effector assembly disposed at a distal end of the shaft, the end effector assembly defining a distal end; and
   a selectively engagable energizable surgical attachment, including:
      an outer sheath defining a proximal end and a distal end and including an internal surface defining a lumen extending longitudinally through the outer sheath, the outer sheath configured for positioning about the shaft of the surgical instrument;
      an energizable rod member coupled to the outer sheath, wherein the outer sheath and the energizable rod member are configured to translate about the shaft of the surgical instrument between a retracted position, wherein the entire outer sheath and the entire energizable rod member are proximally-spaced from the distal end of the end effector assembly, and a deployed position, wherein the outer sheath and the energizable rod member extend distally from the distal end of the end effector assembly, the energizable rod member and the outer sheath rotatable relative to the surgical instrument in both the retracted position and the deployed position;
      a connector attachment disposed towards the proximal end of the outer sheath, the connector attachment electrically coupled to the energizable rod member; and
      at least one o-ring disposed within the lumen of the outer sheath and coupled to the internal surface of the outer sheath, the at least one o-ring configured to establish a fluid-tight seal between the outer sheath and the shaft of the surgical instrument and to bias the outer sheath towards a stationary position relative to the shaft of the surgical instrument,
      the proximal end of the outer sheath of the energizable surgical attachment spaced apart from a distal-most end of the housing of the surgical instrument in both the retracted and deployed positions.

2. The surgical system according to claim 1, wherein the transition of the outer sheath and the energizable rod member between the retracted position and the deployed position is performed manually upon sufficient urging to overcome the bias of the outer sheath towards the stationary position relative to the shaft of the surgical instrument.

3. The surgical system according to claim 1, further including a connector assembly configured to releasably couple to the connector attachment.

4. The surgical system according to claim 3, wherein the connector assembly includes a hand-activated switch and a plug, the plug adapted to connect to a source of energy.

5. The surgical system according to claim 4, wherein the hand-activated switch is configured to couple to the surgical instrument.

6. The surgical system according to claim 1, wherein the at least o-ring possesses an inner diameter less than an outer diameter of the shaft of the surgical instrument.

* * * * *